United States Patent [19]
Schneider et al.

[11] Patent Number: 5,324,721
[45] Date of Patent: Jun. 28, 1994

[54] 3-SUBSTITUTED CEPHALOSPORINS, AND THEIR USE AS MEDICAMENTS

[75] Inventors: Stephan Schneider; Rainer Endermann; Karl-Georg Metzger; Klaus-Dieter Bremm, all of Wuppertal, Fed. Rep. of Germany

[73] Assignee: Bayer Aktiengesellschaft, Leverkusen, Fed. Rep. of Germany

[21] Appl. No.: 762,706

[22] Filed: Sep. 19, 1991

[30] Foreign Application Priority Data

Sep. 28, 1990 [DE] Fed. Rep. of Germany ....... 4030706

[51] Int. Cl.$^5$ ................. C07D 501/34; A61K 31/545
[52] U.S. Cl. ................................... 514/202; 514/206; 540/222; 540/227
[58] Field of Search ................ 514/202, 206; 540/222, 540/221, 227

[56] References Cited

U.S. PATENT DOCUMENTS

| | | | |
|---|---|---|---|
| 4,110,165 | 8/1978 | Cole et al. | 195/80 R |
| 4,460,582 | 7/1984 | Nayler | 540/222 |
| 4,855,418 | 8/1989 | Cook et al. | 540/205 |
| 4,861,769 | 8/1989 | Takaya et al. | 540/222 |
| 4,983,732 | 1/1991 | Blaszczak et al. | 540/222 |
| 5,081,116 | 1/1492 | Nagano et al. | 540/226 |

FOREIGN PATENT DOCUMENTS

| | | |
|---|---|---|
| 0192210 | 8/1986 | European Pat. Off. . |
| 343277 | 11/1989 | European Pat. Off. . |
| 0420608 | 4/1991 | European Pat. Off. . |
| 2517316 | 10/1975 | Fed. Rep. of Germany . |
| 56-104812 | 8/1981 | Japan . |

OTHER PUBLICATIONS

J. Org. Chem. 1989, vol. 54, pp. 20-21.
Tetrahedron, vol. 34, pp. 2233-2243 (1978).
Tetrahedron Letters, vol. 29, No. 47, pp. 6043-6046, 1988.
J. Org. Chem. 1989, 54, pp. 4962-4966.
Nagano et al., "Studies on beta-lactam antibiotics," Chem. Abstracts, vol. 115 (Sep. 1991), pp. 724.
Farina et al., "Palladium catalysis in cephalosporins chemistry," Tetrahedron Letters, vol. 29, No. 46, 1988, pp. 6043-6046.
Bucourt et al., "Cephalosporines a chaines amino-2--thaizolyl-4-acetyles", Tetrahedron Letters, vol. 34, No. 13, 1978, pp. 2233-2243.

*Primary Examiner*—Nicholas S. Rizzo
*Attorney, Agent, or Firm*—Sprung Horn Kramer & Woods

[57] ABSTRACT

The invention relates to new 3-substituted cephalosporins, a process for their preparation and their use as medicaments, in particular as medicaments having antibacterial activitity.

9 Claims, No Drawings

3-SUBSTITUTED CEPHALOSPORINS, AND THEIR USE AS MEDICAMENTS

The invention relates to new 3-substituted cephalosporins, a process for their preparation and their use as medicaments, in particular as medicaments having antibacterial activity.

EP 192,210 A2 discloses 7-substituted cyclopropyloxyiminoacetamido-cephem-carboxylic acids having antibacterial activity.

In the publication JP 56 104,812, cephalosporins of which the 7-position can be substituted by an oximino function and the 3-position can also be substituted by a phenyl ring are encompassed by the width of the claims, no actual representative substance being mentioned.

The invention relates to compounds of the general formula (I)

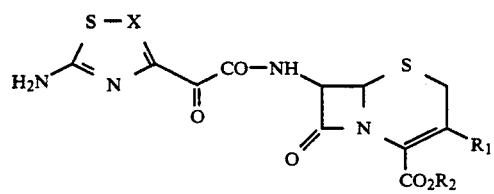

in which
  X represents a nitrogen atom or the —CH group,
  Y represents a group of the formula N—OR$_3$ or CHR$_4$ in which
   R$_3$ denotes hydrogen straight-chain or branched alkenyl, alkinyl or alkyl in each case having up to 8 carbon atoms, where the latter can optionally be substituted by halogen or by protected or unprotected carboxyl or amino,
   R$_4$ denotes hydrogen, aryl having 6 to 10 carbon atoms, protected or unprotected carboxyl, halogen or straight-chain or branched alkoxycarbonyl, alkoxy, alkenyl or alkyl in each case having up to 8 carbon atoms, where the latter can be substituted by halogen, hydroxyl, nitro, cyano, carboxyl or by straight-chain or branched alkoxy or alkoxycarbonyl in each case having up to 6 carbon atoms,
  R$_1$ represents thienyl, furyl or phenyl which are optionally monosubstituted to trisubstituted by identical or different halogen, trifhoromethyl, trifhoromethoxy or hydroxyl substituents or by a group of the formula —NR$_5$R$_6$ in which
   R$_5$ and R$_6$ are identical or different and denote hydrogen, straight-chain or branched alkyl having up to 8 carbon atoms or phenyl,
  or are substituted by straight-chain or branched alkoxy or alkyl in each case having up to 8 carbon atoms, where the latter can be substituted by hydroxyl, halogen or by straight-chain or branched alkoxy having up to 6 carbon atoms,
  R$_2$ represents hydrogen, or represents a carboxyl protecting group or represents an ester radical which can be cleaved in vivo, and their pharmaceutically tolerable salts.

Because of the presence of double bonds (=Y), the compounds of the general formula (I) according to the invention can occur as pure syn- or anti-isomers or as mixtures of isomers. The syn-isomers of the compounds of the general formula (I) according to the invention are preferred.

Both the isomer mixtures and the syn- and anti-form of the compounds according to the invention can be employed for the treatment of bacterial infectious diseases.

The compounds of the general formula (I) can be present as free acids, esters, as internal salts or as non-toxic pharmaceutically tolerable salts of the acidic carboxyl groups such as sodium, potassium, magnesium, calcium, aluminium or ammonium salts, with amines such as di- and tri-lower alkylamines, procaine, dibenzylamine, N,N'-di-benzylethylenediamine, N-benzyl-β-phenyl-ethylamine, N-methyl- and N-ethylmorpholine, 1-ephenamine, dihydroabietylamine, N,N'-bis-dehydroabietylethylenediamine, N-lower alkylpiperidine and other amines which can be used for the formation of salts of penicillins and cephalosporins.

Examples of non-toxic, pharmaceutically tolerable salts of the basic amino groups with inorganic or organic acid radicals which can preferably be mentioned are chloride, bromide, iodide, sulphate, hydrogen sulphate, phosphate, carbonate, hydrogen carbonate, or sulphonates such as methylsulphonate, ethanesulphonate, toluenesulphonate, benzenesulphonate, naphthalenedisulphonate, or carboxylates such as acetate, formate, oxalate, tartrate, citrate, maleate, fumarate, benzoate, succinate or lactate.

Amino or oxime protecting group in the context of the abovementioned definition in general represents a protecting group customary in β-lactam chemistry from the series comprising: tert-butoxycarbonyl, benzyloxycarbonyl, 2-nitrobenzyloxycarbonyl, 4-nitrobenzyloxycarbonyl, phenylacetyl, allyloxycarbonyl, 2,4-dimethoxybenzyloxycarbonyl, allyloxymethyl, bis-(4-methoxyphenyl)-methyl, 2-(methylthiomethoxy)ethoxycarbonyl, trimethyl-, triethyl-, triphenylsilyl, trityl, tert-butyl-dimethylsilyl, tert-butyldiphenylsilyl, [2-(trimethylsilyl)ethoxy]methyl, 1-methyl-2-benzoylvinyl, 1-methyl-2-methoxyvinyl, 1-methyl-2-acetylvinyl, 1-methyl-2(methoxybenzoyl)-vinyl, 1-methyl-2-(2,6-dimethoxybenzoyl)vinyl and 1-methyl-2-ethoxycarbonyl-vinyl.

Carboxyl protecting group in the context of the above-mentioned definition represents the carboxyl protecting group customary in β-lactam chemistry. Easily cleavable groups can preferably be mentioned, such as, for example: tert-butyl, 2,2,2-trichloroethyl, diphenylmethyl, triphenylmethyl, acetoxymethyl, allyl, benzyl, 4-methoxyphenyl, 4-nitrobenzyl, 2-nitrobenzyl, 4-methoxybenzyl, 2,4-dimethoxybenzyl, trimethylsilylethyl, trimethylsilyl, tert-butyl-dimethylsilyl, acetonyl, 1-phenoxyethyl or 2-methyl-2-propenyl.

If R$_2$ represents an ester radical which can be easily cleaved in vivo, pharmaceutically tolerable ester radicals which are easily hydrolysed in vivo to give free carboxyl groups (R$_2$=H) are meant by this.

Such ester radicals are well-known in the β-lactam field. In most cases, they improve the absorption properties of the β-lactam compounds. The R$^2$ radical should additionally be of a type such that it imparts pharmaceutically acceptable properties to a compound of the formula (I) and on cleavage in vivo releases pharmaceutically acceptable fragments.

Examples of such groups are found in German Offenlegungsschrift 2,517,316. Preferred ester groups which can be cleaved in vivo are those of the following formulae:

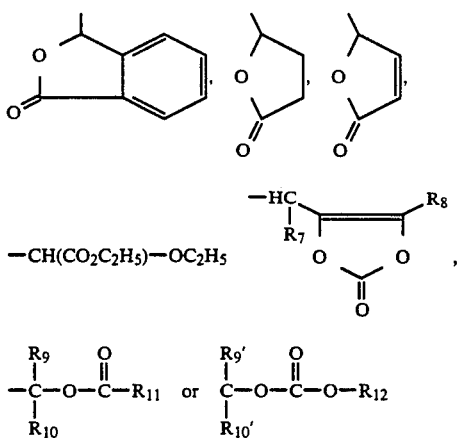

—CH(CO₂C₂H₅)—OC₂H₅

$$-\underset{\underset{R_{10}}{|}}{\overset{\overset{R_9}{|}}{C}}-O-\overset{\overset{O}{\|}}{C}-R_{11} \quad \text{or} \quad -\underset{\underset{R_{10'}}{|}}{\overset{\overset{R_{9'}}{|}}{C}}-O-\overset{\overset{O}{\|}}{C}-O-R_{12}$$

in which $R_7$ and $R_8$ are identical or different and denote hydrogen, phenyl or straight-chain or branched alkyl having up to 4 carbon atoms, $R_9$, $R_{9'}$ and $R_{10'}$ are identical or different and denote hydrogen or straight-chain or branched alkyl having up to 4 carbon atoms, $R^{11}$ denotes straight-chain or branched alkyl having up to 6 carbon atoms, $R^{12}$ denotes straight-chain or branched alkyl having up to 6 carbon atoms or cyclohexyl.

Preferred compounds of the general formula (I) are those in which

X represents a nitrogen atom or the —CH group,

Y represents a group of the formula N—OR₃ or CHR₄, in which $R^3$ denotes hydrogen or straight-chain or branched alkyl having up to 6 carbon atoms, which is optionally substituted by fluorine, chlorine, bromine or protected or unprotected carboxyl or amino, $R^4$ denotes hydrogen, phenyl, carboxyl, fluorine, chlorine, bromine or straight-chain or branched alkoxy, alkoxycarbonyl or alkyl in each case having up to 6 carbon atoms, where the latter can be substituted by fluorine, chlorine, bromine, hydroxyl, carboxyl or by straight-chain or branched alkoxy or alkoxycarbonyl in each case having up to 4 carbon atoms, $R_1$ represents thienyl, furyl or phenyl, which are optionally monosubstituted or disubstituted by identical or different fluorine, chlorine Or bromine substituents, or by a group of the formula —NR⁵R⁶, in which $R_5$ and $R_6$ are identical or different and denote hydrogen or straight-chain or branched alkyl having up to 6 carbon atoms, or are substituted by straight-chain or branched alkoxy or alkyl in each case having up to 6 carbon atoms, where the latter can be substituted by hydroxyl, fluorine, chlorine or by straight-chain or branched alkoxy having up to 4 carbon atoms, $R_2$ represents hydrogen, or represents methyl, ethyl, tert-butyl, 2-chloroethyl, 2,2,2-trichloroethyl, cyanoethyl, diphenylmethyl, triphenylmethyl, acetoxymethyl, allyl, benzyl, 4-methoxybenzyl, 2,4-dimethoxybenzyl, 1-phenoxyethyl, 2-methyl-2-propenyl, 4-nitrobenzyl, 2-nitrobenzyl, trimethylsilylethyl or tert-butyl-dimethylsilylethyl, or represents a radical of the formula

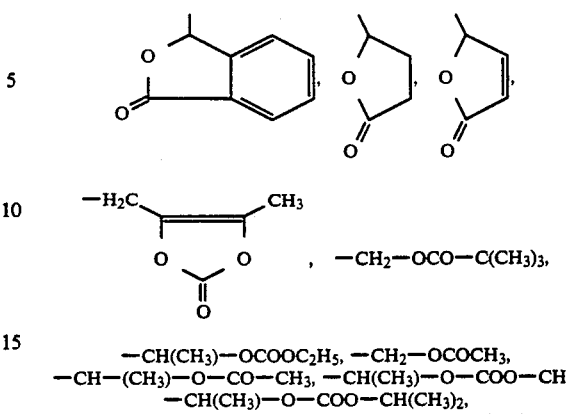

—CH(CH₃)—OCOOC₂H₅, —CH₂—OCOCH₃,
—CH—(CH₃)—O—CO—CH₃, —CH(CH₃)—O—COO—CH₃,
—CH(CH₃)—O—COO—CH(CH₃)₂,
—CH(CH₃)—O—COO—C₆H₁₁ or —CH(CO₂C₂H₅)—OC₂H₅ and their pharmaceutically tolerable salts.

Particularly preferred compounds of the general formula (I) are those in which

X represents a nitrogen atom or the —CH group,

Y represents a group of the formula N—OR₃ or —CHR₄, in which $R_3$ denotes hydrogen or straight-chain or branched alkyl having up to 4 carbon atoms, which is optionally substituted by fluorine, chlorine or by protected or unprotected carboxyl or amino, $R_4$ denotes hydrogen or straight-chain or branched alkoxy or alkyl in each case having up to 4 carbon atoms, where the latter can be substituted by hydroxyl, carboxyl, methoxy, ethoxy or propoxy, $R_1$ represents thienyl, furyl or phenyl, which are optionally monosubstituted or disubstituted by identical or different fluorine, chlorine, bromine or amino substituents or by straight-chain or branched alkoxy, alkoxycarbonyl or alkyl in each case having up to 4 carbon atoms, where the latter can be substituted by hydroxyl, fluorine, chlorine, methoxy or ethoxy, $R_2$ represents hydrogen, or represents a radical of the formula

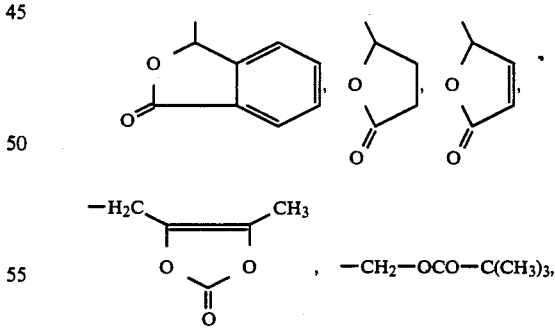

—CH(CH₃)—OCOOC₂H₅, —CH₂—OCOCH₃,
—CH—(CH₃)—O—CO—CH₃, —CH(CH₃)—O—COO—CH₃,
—CH(CH₃)—O—COO—CH(CH₃)₂,
—CH(CH₃)—O—COO—C₆H₁₁ or —CH(CO₂C₂H₅)—OC₂H₅ and their pharmaceutically tolerable salts.

The sodium salts are very particularly preferred.

A process for the preparation of the compounds of the general formula (I) according to the invention has furthermore been found, characterised in that compounds of the general formula (II) 0

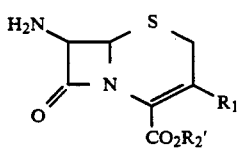

(II)

in which

R₁ has the abovementioned meaning and $R_2'$ represents one of the abovementioned carboxyl protecting groups, in particular p-methoxybenzyl, are reacted, if appropriate also with activation of the amino function, with compounds of the general formula (III)

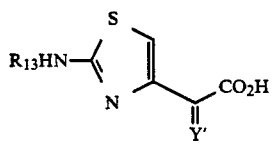

(III)

in inert solvents, if appropriate with activation of the carboxyl group in the presence of an auxiliary, initially to give the compounds of the general formula (IV)

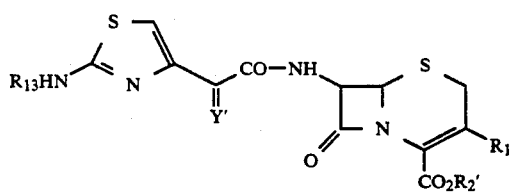

(IV)

in which $R_1$, $R_2$, $R_{13}$ and $Y'$ have the abovementioned meaning, and the protecting groups $R_2$, $R^{3'}$, $R_{4'}$ ($Y'$) and $R_{13}$ are then removed by a customary method, if appropriate in 2 steps, and the desired salts are prepared or the free acids are prepared from the salts.

The process according to the invention can be illustrated by way of example by the following reaction scheme:

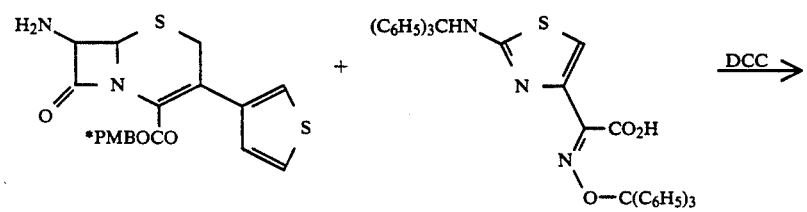

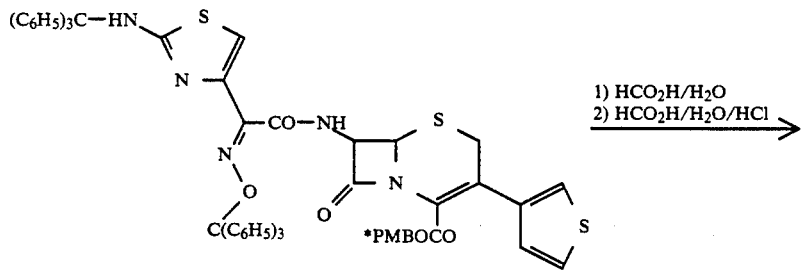

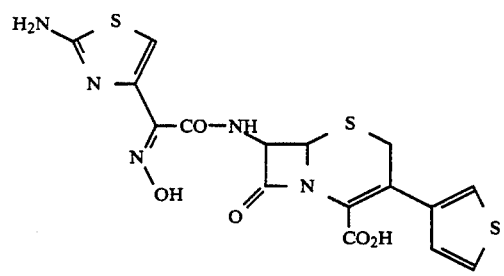

*PMB = p-Methoxybenzyl in which $Y_1$ represents one of the abovementioned groups N—OR₃' or CHR₄', in which R₃' has the abovementioned meaning of R³ or represents one of the abovementioned oxime protecting groups, in particular the trityl radical, R₄' has the abovementioned meaning of R₄ or represents protected carboxyl and R₁₃ also represents one of the abovementioned amino protecting groups, preferably BOC or the trityl radical, Suitable solvents are all solvents which do not change under the reaction conditions. These preferably include ethers such as, for example, diethyl ether, dioxane or tetrahydrofuran, or chlorohydrocarbons such as methylene chloride, chloroform or tetrachloromethane, or amides such as dimethylformamide or hexamethylphosphoric triamide, or acetonitrile or acetone. It is also possible to employ mixtures of the solvents mentioned. Methylene chloride is preferred.

The condensation is in general carried out in a temperature range from 0° C. to +60° C., preferably at room temperature and at normal pressure.

The activation of the carboxyl group in the compounds of the general formula (III) is in general carried out by conversion into a mixed anhydride using esters of chloroformic acid or sulphonic acid derivatives, such as, for example, ethyl chloroformate, isobutyl chloroformate or methanesulphonyl chloride, by conversion into the corresponding acid halide, or by conversion into an activated ester, for example using N-hydroxybenzotriazole or dicyclohexylcarbodiimide. Reaction with ethyl chloroformate or methanesulphonyl chloride is preferred.

The activation of the amino function of the compounds of the general formula (II) is carried out by a customary method, for example by conversion into the corresponding silyl derivatives by reaction with bis(-trimethylsilyl)-acetamide, N-trimethylsilylacetamide or bis(trimethylsilyl)urea.

Auxiliaries employed are preferably condensing agents which can also be bases, in particular if, for example, the carboxyl group is present in activated form as the anhydride. Those preferably employed here are the customary condensing agents such as carbodiimides, for example N,N'-diethyl-, N,N'-dipropyl-, N,N'-diisopropyl- or N,N'-dicyclohexylcarbodiimide, N-(3-dimethylaminoisopropyl)-N'-ethylcarbodiimide hydrochloride, or carbonyl compounds such as carbonyldiimidazole, or 1,2-oxazolium compounds such as 2-ethyl-5-phenyl-1,2-oxazolium-3-sulphonate or 2-tert-butyl-5-methyl-isoxazolium perchlorate, or acylamino compounds such as 2-ethoxy-l-ethoxycarbonyl-1,2-dihydroquinoline, or propanephosphonic anhydride, or isobutyl chloroformate, or benzotriazolyloxy-tris(dimethylamino)phosphonium hexafluorophosphate, or as bases alkali metal carbonates, for example sodium carbonate or potassium carbonate or sodium hydrogen carbonate or potassium hydrogen carbonate, or organic bases such as trialkylamines, for example triethylamine, N-ethylmorpholine or N-methylpiperidine.

The removal of the protecting groups is carried out by a customary method, in the case of the oximes if desired successively, either using organic acids, such as, for example, formic acid, if appropriate in the presence of water or in the presence of water and a protonic acid, such as, for example, hydrochloric acid, preferably using formic acid and water or formic acid, water and hydrochloric acid.

In the case in which $R_3 \neq H$, it is moreover possible to remove the amino protecting group $R_{13}$, the carboxyl protecting groups $R_{2'}$ and the protecting groups $R^3$ and $R^{4'}$ using trifluoroacetic acid, if appropriate in one step.

The removal of the protecting groups is in general carried out in a temperature range from 0° C. to +80° C., preferably at room temperature.

The removals can be carried out both at normal pressure and at elevated or reduced pressure (for example 0.5 to 5 bar), preferably at normal pressure.

The compounds of the general formula (II) are in some cases encompassed by the width of the claims of other publications, such as, for example, in EP 192,210 A2 and can be prepared in analogy to processes known from the literature [cf. U.S. Pat. No. 4,855,4 18; Tetrahedron Lett., vol. 29, No. 47, 6043–6046, 1988]by reacting, for example, p-methoxybenzyl 7-phenacetylamino-3-trifluoromethanesulphonyl-3-cephem-4-carboxylate of the formula (V)

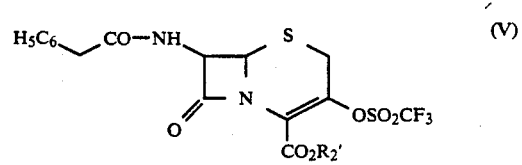

in which $R_{2'}$ has the abovementioned meaning, with compounds of the general formula (VI)

in which $R_1$ has the abovementioned meaning and

Z represents an organotin radical defined in the following, in aprotic polar solvents, in the presence of metal halides, phosphines and a catalyst, to give compounds of the general formula (VII)

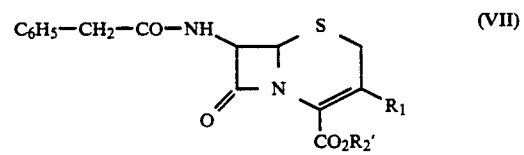

in which $R_1$ and $R_{2'}$ have the abovementioned meaning, and in a last step deblocking the amino function according to a customary method, for example by the action of the system 1.) $PCl_5$/pyridine/methylene chloride and 2.) $HN(C_2H_5)_2$/methanol.

Suitable organotin radicals ( Z ) are, for example, tri-methylstannyl, triethylstannyl or tributylstannyl. Tri-n-butylstannyl is preferred.

Suitable metal halides are zinc, lithium and magnesium halides, such as, for example, $ZnCl_2$, $ZnBr_2$, LiCl, LiBr, $MgCl_2$. or $MgBr_2$. $ZnCl_2$ is preferred.

Suitable catalysts are Pd(O) and (II) complexes, such as, for example, bis (dibenzylidene-acetonyl ) palladium [(Pd/dba)$_2$], Pd$_2$dba$_3$×CHCl$_3$ or Pd(OAc)$_2$·Pd$_2$·dba$_3$×CHCl$_3$ is preferred.

Suitable aprotic polar solvents are, for example, acetonitrile, dimethyl sulphoxide (DMSO), dimethylformamide (DMF), or ethers such as glyme, dioxane or THF, or acetone, hexamethylphosphoramide, or N-methylpyrrolidone or 1-methyl-2-pyrrolidone. N-Methylpyrrolidone is preferred.

Phosphines which can be employed are, for example, triphenyl phosphine, tri-( 3-fluorophenyl )-phosphine, diphenylmethylphosphine, tributylphosphine, tri-( 2-thienyl )phosphine or tri-( 2-furyl )phosphine. Tri-(2-furyl)phosphine is preferred.

The reaction is carried out in a temperature range from −30° C. to +90° C., preferably at room temperature and normal pressure.

The compound of the general formula (V) is known per se [J. Org. Chem. 1989, 54, 4962–4966].

The compounds of the general formula (VI) are known per se and can be prepared and employed according to processes known from the literature [cf. EP 343,277 A1].

The compounds of the general formula (VII) are new with respect to the abovementioned definition of $R^1$ but can be prepared in analogy to known processes [cf. J. Org. Chem., Vol. 54, No. 20, 1989].

The compounds of the general formula (III) are known per se or can be prepared by a customary method [cf. Tetrahedron, Vol. 34, 2233–2243].

The compounds of the general formula (IV) are new and can be prepared by the abovementioned process.

The compounds of the general formula (I) according to the invention have a broad antibacterial spectrum against Gram-positive and Gram-negative microorganisms and a low toxicity. These properties make possible their use as chemotherapeutic active compounds in human and veterinary medicine.

The compounds according to the invention are active against a very broad spectrum of microorganisms. Gram-negative and Gram-positive bacteria and bacteria-like microorganisms can be controlled with their aid and the diseases caused by these pathogens can be prevented, ameliorated and/or cured.

The compounds according to the invention are particularly active against bacteria and bacteria-like microorganisms. They are therefore particularly well suited in human and veterinary medicine for the prophylaxis and chemotherapy of local and systemic infections which are caused by such pathogens.

The minimum inhibitory concentrations (MIC) were determined by the serial dilution method on iso-sensitest agar (oxoid). A series of agar plates which contained concentrations of the active compound decreasing in double dilutions in each case were prepared for each test substance. The agar plates were inoculated using a multipoint inoculator (Denley). For the inoculation, overnight cultures of the pathogens were used which were previously diluted in such a way that each inoculation point contained about $10^4$ colony-forming particles. The inoculated agar plates were incubated at 37° C. and the bacterial growth was read off after about 20 hours. The MIC value ($\mu$g/ml) indicates the lowest active compound concentration at which no bacterial growth could be detected with the naked eye.

USE EXAMPLE

MIC values: agar dilution/multipoint

| Microorganisms | XVIII | XVI |
|---|---|---|
| E. coli T7 | 2 | 1 |
| E. coli Neumann | 0.5 | 0.5 |
| E. coli 183/58 | 4 | 4 |
| E. coli F14 | 2 | 2 |
| E. coli C 165 | 2 | 2 |
| E. coli 4322 | <0.25 | 0.5 |
| Klebs. 57 USA | <0.25 | 0.5 |
| Klebs. 63 | 2 | 2 |
| Klebs. 1852 | 2 | 2 |
| Klebs. 6097 | 2 | 2 |
| Serratia 16001 | 4 | 4 |
| Serratia 16002 | 16 | 16 |
| Provid. 12012 | <0.25 | <0.25 |
| Prot. morg. 932 | 32 | 128 |
| Prot. vulg. 9032 | 0.5 | 4 |
| Prot. vulg. 1017 | <0.25 | 0.5 |
| Prot. vulg. N6 | 16 | 4 |
| Prot. rettg. 10007 | 2 | 2 |
| Prot. mir. 1235 | 1 | 1 |
| Staph. aur. 1756 | 64 | 128 |
| Staph. aur. 133 | 1 | 1 |
| Staph. aur. 25455 | 1 | 1 |
| Staph. aur. 25470 | 1 | 2 |
| Strepto. faec. 27101 | 128 | >128 |
| Strepto. faec. 113 | 2 | 2 |
| Enterococ. 9790 | 128 | >128 |
| Enterococ. 27158 | 2 | 2 |
| Psdm. aerug. F41 | >128 | >128 |
| Psdm. aerug. Walter | >128 | >128 |
| Psdm. aerug. 7035 | >128 | >128 |
| Psdm. aerug. 7451 | >128 | >128 |
| Enterob. cl. 5605 | >128 | >128 |
| Enterob. cl. 5744 | 4 | 4 |
| Acinetop. 14061 | 32 | 32 |

The present invention includes pharmaceutical preparations which contain one or more compounds according to the invention in addition to non-toxic, inert pharmaceutically suitable excipients or which consist of one or more active compounds according to the invention, and processes for the production of these preparations.

The active compound(s) can optionally also be present in microencapsulated form in one or more of the abovementioned excipients.

The therapeutically active compounds should preferably be present in the abovementioned pharmaceutical preparations in a concentration of about 0.1 to 99.5, preferably of about 0.5 to 95% by weight of the total mixture.

The abovementioned pharmaceutical preparations can also contain other pharmaceutical active compounds in addition to the compounds according to the invention.

In general, it has proved advantageous both in human and in veterinary medicine to administer the active compound(s) according to the invention in total amounts of about 0.5 to about 500, preferably 5 to 100, mg/kg of body weight every 24 hours, if appropriate in the form of several individual doses, to achieve the desired results. An individual dose preferably contains the active compound(s) according to the invention in amounts of about 1 to about 80, in particular 3 to 30, mg/kg of body weight.

The new compounds can be combined in the customary concentrations and preparations together with the feed and/or lactamase inhibitors, for example with penicillins which are particularly resistant to penicillinase and clavulanic acid. Such a combination would be, for example, that with oxacillin or dicloxacillin.

The compounds according to the invention can also be combined with aminoglycoside antibiotics, such as, for example, gentamicin, sisomicin, kanamicin, amicacin or tobramicin for the purpose of extending the spectrum of action and in order to achieve an increase in action.

$^1$H-NMR data exist for all compounds.

STARTING COMPOUNDS

EXAMPLE I (2-Methoxymethyl-3-thienyl )-tri-n-butyl-stannane

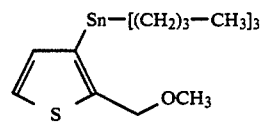

19.2 g (150 mmol) of 2-methoxymethyl-thiophene are added dropwise at −78° C. to a solution of 150 mmol of n-butyllithium in 500 ml of THF. The mixture is allowed to warm to 0° C. and is cooled again to −78° C. after 5 min, and 43.4 ml (160mmol) of tributyltin chloride are added. The cooling bath is removed and the mixture is stirred overnight at room temperature. 500 ml of saturated ammonium chloride solution are added for working up. The mixture is extracted with ether, the combined organic phases are dried and the solvent is removed. After chromatography on silica gel using petroleum ether, 17.7 g (28% of theory) of the title compound are obtained.

EXAMPLE 2

4-Bromo- 2-methoxymethyl-thiophene

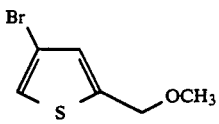

A mixture of 48.2 g (0.25 mol) of 4-bromo-2-hydroxymethyl-thiophene and 15.7 ml (0.25 mol) of methyl iodide is added dropwise to a suspension of 7.5 g (0.25 mol) of 80% strength sodium hydride. The mixture is stirred overnight, the solvent is stripped off, the residue is partitioned between methylene chloride and water (1.0 l each), and the organic phase is separated off and dried using sodium sulphate. After the removal of the solvent, the residue is chromatographed on silica gel using toluene/petroleum ether (1:1).

Yield: 48.2 g (93% of theory)

EXAMPLE 3

(4-Bromo-2-methoxymethyl- 3-thienyl ) -tri-n-butyl-stannane

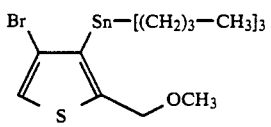

31.1 g ( 150 mmol ) of the compound from Example 2 are added dropwise at −78° C. under argon to a solution of 150 mmol of n-butyllithium. The mixture is allowed to warm to −40° C. and is cooled again to −78° C. after 20 min, and 43.4 ml (160 mmol) of tributyltin chloride are added. The solution is stirred overnight at room temperature and saturated ammonium chloride solution and methylene chloride are added. The organic phase is separated off and dried using sodium sulphate. After distilling off the solvent, the residue is chromatographed on silica gel using petroleum ether.

Yield: 19.5 g (26% of theory)

EXAMPLE 4 p-Methoxybenzyl 7β-phenacetylamino- 3- ( 2-thienyl ) -3-cephem-4-carboxylate

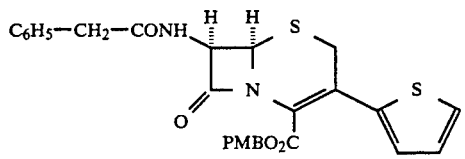

4.68 g (8.0 mmol) of p-methoxybenzyl 7-phenacetylamino-3-trifluoromethanesulphonyl-3-cephem-4-carboxylate are allowed to react under argon overnight at room temperature with 2.98 g (8.0 mmol) of 2-thienyl-tri-n-butylstannane, 1.90 g (13.9 mmol) of zinc chloride, 0.34 g (1.46 mmol) of tri-2-furyl-phosphine and 0.35 g (0.34 mmol) of tris-(dibenzylideneacetone)-dipalladiumchloroform in 130 ml of anhydrous N-methylpyrrolidone. The mixture is then poured into 400 ml of water and the precipitate deposited is filtered off with suction. The residue, dissolved in 400 ml of methylene chloride, is dried using sodium sulphate and chromatographed on silica gel using toluene/ethyl acetate (5:1) after the removal of the solvent.

Yield: 2.52 g (61% of theory)

The following compounds are prepared in analogy to the procedure of Example 4:

| Example No.: | $R_1$ |
|---|---|
| 5 | ![furan with methyl, O at bottom] |
| 6 | ![furan with O at top] |
| 7 | ![phenyl] |
| 8 | ![4-fluorophenyl] |
| 9 | ![3-fluorophenyl] |
| 10 | ![2-fluorophenyl] |
| 11 | ![3-methylphenyl, CH₃] |
| 12 | ![4-methylphenyl, CH₃] |
| 13 | ![2-methoxyphenyl, OCH₃] |

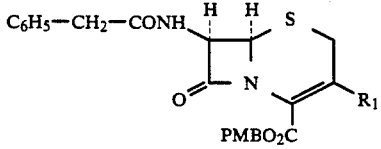

| Example No.: | R₁ |
|---|---|
| 14 | 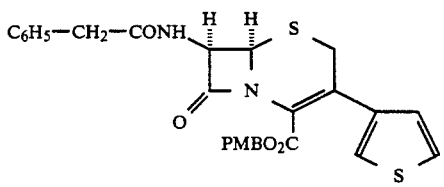 |
| 15 | |

EXAMPLE 16 p-Methoxybenzyl 7β-phenacetylamino-3-(3-thienyl)-3-cephem-4-carboxylate

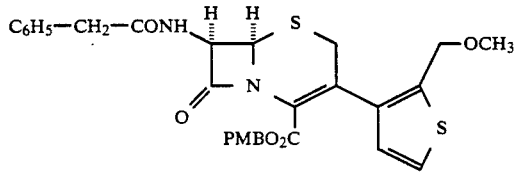

In analogy to the procedure of Example 4, 2.69 g (65% of theory) of the title compound are prepared from 2.98 g (8.0 mmol) of 3-thienyl-tri-n-butyl-stannane.

EXAMPLE 17 p-Methoxybenzyl 3-(2-methoxymethyl-3-thienyl)-7β-phenacetyl-amino-3-cephem-4-carboxylate

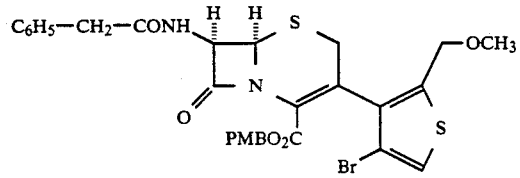

In analogy to the procedure of Example 4, 1.9 g (42% of theory) of the title compound are prepared from 3.3 g (8.0 mmol) of the compound from Example 1.

EXAMPLE 18 p-Methoxybenzyl 3-(4-bromo-2-methoxymethyl-3-thienyl)-7β-phenacetyl-amino-3-cephem-4-carboxylate In analogy to the procedure of Example 4, 1.20 g (27% of theory) of the title compound are prepared from 3.34 g (8.0 mmol) of the compound from Example 3.

EXAMPLE 19 p-Methoxybenzyl 7β-amino-3-(2-thienyl)-3-cephem-4-carboxylate

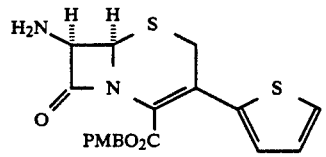

2.0 g (9.7 mmol) of phosphorus pentachloride are added at −20° C. to a solution of 2.5 g (4.8 mmol) of the compound from Example 4 and 1.0 ml (12.4 mmol) of pyridine in 55 ml of anhydrous methylene chloride. The mixture is stirred at −20° C. for 5 min, at 0° C. for 10 min and at 15° C. for 1 h, and is then cooled to −78° C. 42 ml of methanol cooled to −78° C. are rapidly added. The solution is stirred at −78° C. for 5 min, at 0° C. for 10 min and at 15° C. for 25 min. After cooling to −15° C., 0.56 ml (5.4 mmol) of diethylamine is added and the mixture is kept at this temperature for 10 min. It is poured into 150 ml of saturated sodium hydrogen carbonate solution for working up and the mixture is extracted with methylene chloride. The combined organic phases are washed with sodium hydrogen carbonate solution and water, dried with sodium sulphate and concentrated. The residue is chromatographed on silica gel using toluene/ethyl acetate.

Yield: 1.6 g (86% of theory)

The following compounds were prepared in analogy to the procedure of Example 19:

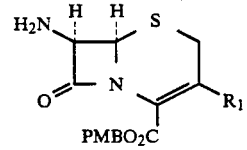

| Example No.: | R₁ |
|---|---|
| 20 |  |
| 21 | 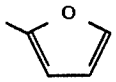 |
| 22 | 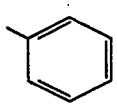 |
| 23 | 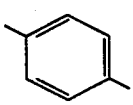 |
| 24 | 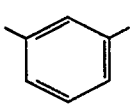 |

-continued

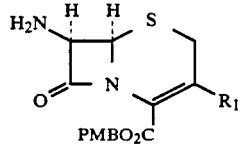

| Example No.: | R₁ |
|---|---|
| 25 | 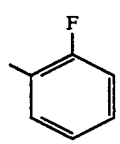 |
| 26 | 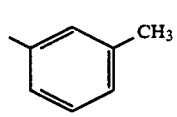 |
| 27 | 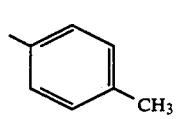 |
| 28 | 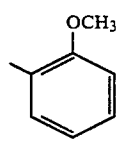 |
| 29 | 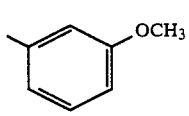 |
| 30 | 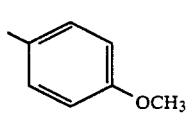 |

EXAMPLE 31 p-Methoxybenzyl 7β-amino-3-(3-thienyl)-3-cephem-4-carboxylate

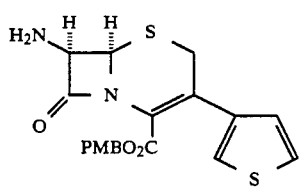

In analogy to the procedure of Example 19, 1.65 g (80% of theory) of the title compound are prepared from 2.65 g (5.1 mmol) of the compound from Example 16.

EXAMPLE 32 p-Methoxybenzyl 7β-amino-3-(2-methoxymethyl-3-thienyl)-3-cephem-4-carboxylate

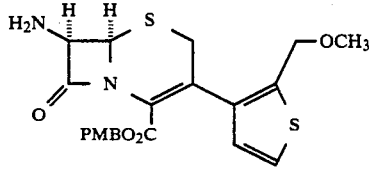

In analogy to the procedure of Example 19, 1.1 g (73% of theory) of the title compound are obtained from 1.9 g (3.4 mmol) of the compound from Example 17.

EXAMPLE 33 p-Methoxybenzyl 7β-amino-3-(4-bromo-2-methoxymethyl-3-thienyl)-3-cephem-4-carboxylate

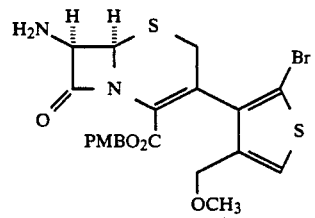

In analogy to the procedure of Example 19, 0.89 g (70% of theory) of the title compound is obtained from 1.55 g (2.4 mmol) of the compound from Example 18.

EXAMPLE 34 p-Methoxybenzyl 7β-[2-(2-t-butyloxycarbonylamino-4-thiazolyl)-2-syn-methoxyimino-acetylamino ]-3-(2-thienyl)-3-cephem-4-carboxylate

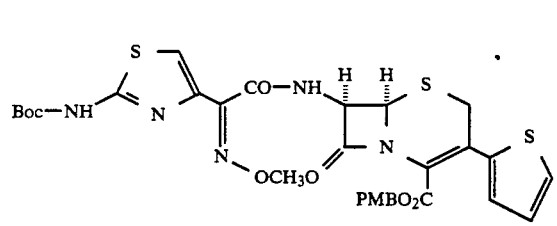

A solution of 0.50 g (1.2 mmol) of the compound from Example 19, 1.14 g ( 3.8 mmol) of 2-(2-t-butyloxycarbonyl-amino-4-thiazolyl)-syn-2-methoxyiminoacetic acid and 0.85 g (4.1mmol) of dicyclohexylcarbodiimide in 40 ml of acetonitrile is stirred overnight. The mixture is concentrated and chromatographed on silica gel using toluene/ethyl acetate (8:1).

Yield: 430 mg (51% of theory)

The following compounds were prepared in analogy to the procedure of Example 34:

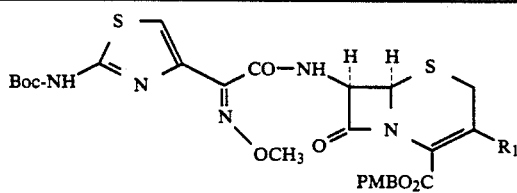

| Example No.: | R₁ |
|---|---|
| 35 | 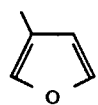 |
| 36 | 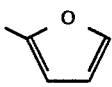 |
| 37 | 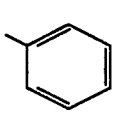 |
| 38 | 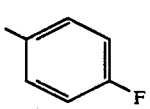 |
| 39 | 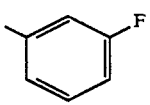 |
| 40 | 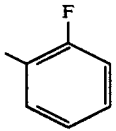 |
| 41 | 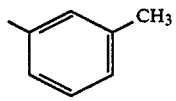 |
| 42 | 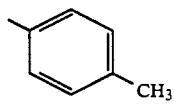 |

-continued

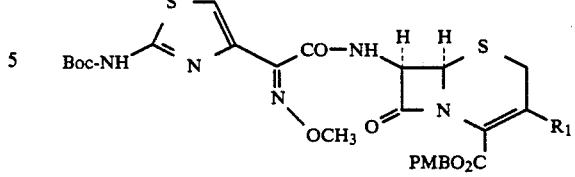

| Example No.: | R₁ |
|---|---|
| 43 | 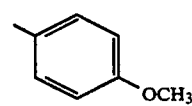 |

EXAMPLE 44 p-Methoxybenzyl 7β-[2-(2-t-butyloxycarbonylamino-4-thiazolyl)-2-syn-methoxyimino-acetylamino]-3-1-(3-thienyl)-3-cephem-4-carboxylate

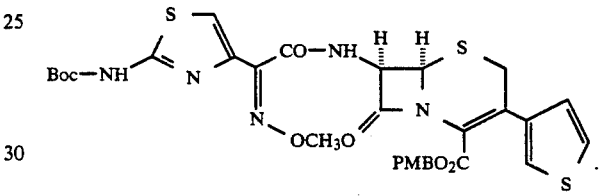

In analogy to the procedure of Example 34, 0.75 g (44% of theory) of the title compound is obtained from 1.00 g (2.5 mmol) of the compound from Example 31.

EXAMPLE 45 p-Methoxybenzyl 7β-[2- (2-t-butyloxycarbonylamino-4-thiazolyl )-2-syn-methoxyimino-acetylamino]-3-(2-methoxymethyl-3-thienyl)-3-cephem-4-carboxylate

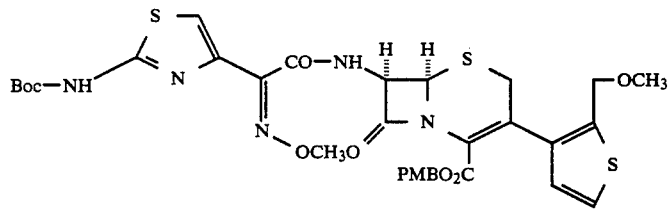

In analogy to the procedure of Example 34, 132 mg (37% of theory) of the title compound are obtained from 220 mg (0.49 mmol) of the compound from Example 32.

EXAMPLE 46 p-Methoxybenzyl 3-(2-thienyl)-7β-[2-(2-tritylamino-4-thiazolyl)-2-syn-trityloxyimino-acetylamino]-3-cephem-4-carboxylate

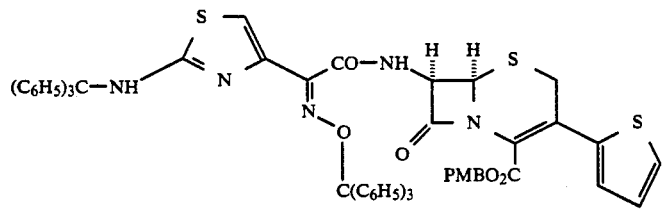

A solution of 3.36 g (5.0 mmol) of 2-(2-tritylamino-4-thiazolyl)-2-syn-trityloxyimino-acetic acid in 50 ml of methylene chloride is stirred at room temperature for 2 h with 1.33 g (6.5 mmol) of dicyclohexylcarbodiimide. 1.00 g (2.5 mmol) of the compound from Example 19 is added and the mixture is stirred overnight at room temperature. After distilling off the solvent, the residue is chromatographed on silica gel using toluene/ethyl acetate (99:1).

Yield: 1.12 g (45% of theory)

The following compounds were prepared in analogy to the procedure of Example 46:

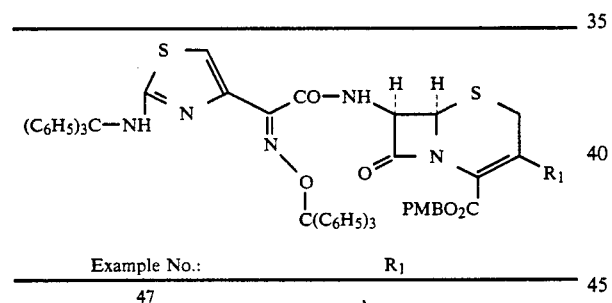

| Example No.: | $R_1$ |
|---|---|
| 47 | 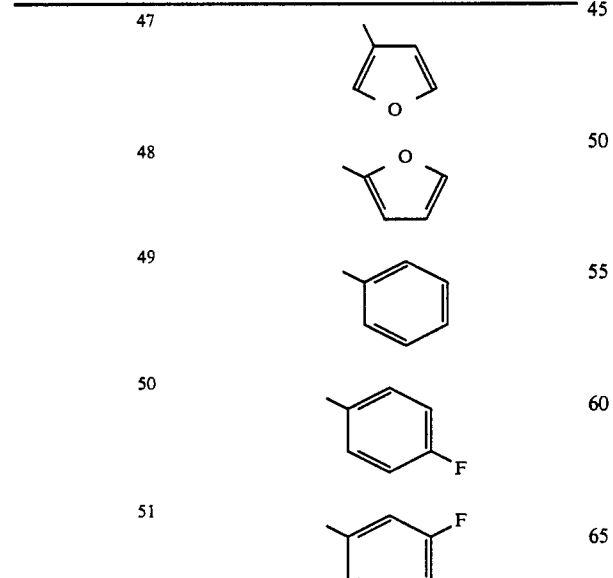 |
| 48 | |
| 49 | |
| 50 | |
| 51 | |

-continued

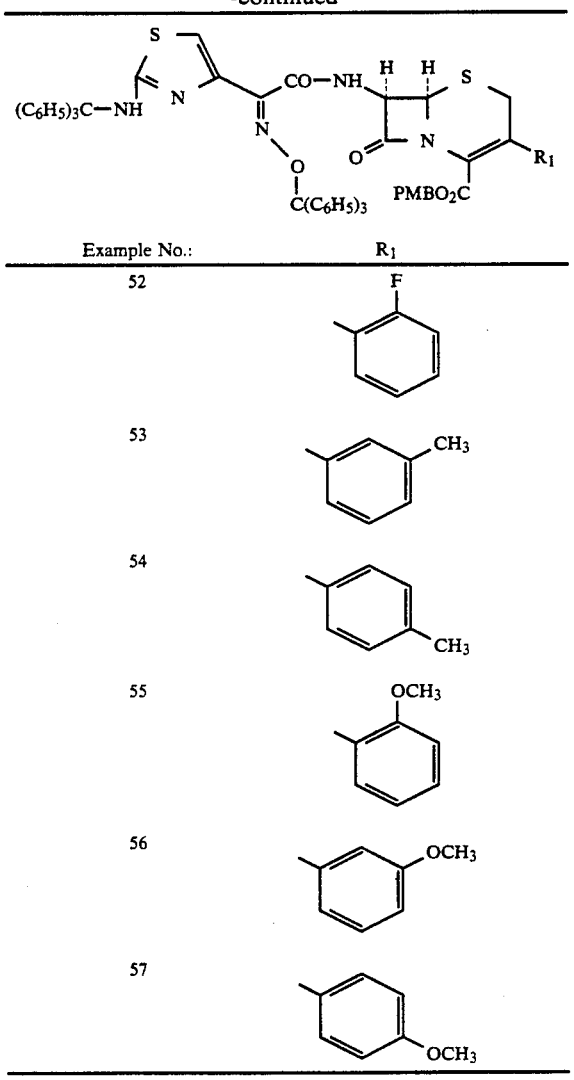

| Example No.: | $R_1$ |
|---|---|
| 52 | |
| 53 | |
| 54 | |
| 55 | |
| 56 | |
| 57 | |

EXAMPLE 58 p-Methoxybenzyl 3-(3-thienyl)-7β-[2-(2-tritylamino-4-thiazolyl)-2-syn-trityloxyimino-acetylamino]-3-cephem-4-carboxylate

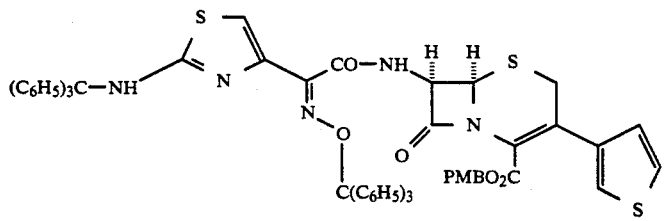

In analogy to the procedure of Example 46, 1.53 g (58% of theory) of the title compound are prepared from 1.00 g (2.5 mmol) of the compound from Example 31.

EXAMPLE 59 p-Methoxybenzyl 3-(2-methoxymethyl-3-thienyl)-7β-[2-(2-tritylamino-4-thiazolyl)-2-syn-trityloxyimino-acetyl-amino]-3-cephem-4-carboxylate

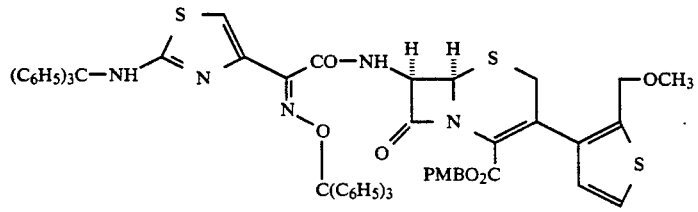

In analogy to the procedure of Example 46, 708 mg (33% of theory) of the title compound are prepared from 870 mg (1.95 mmol) of the compound from Example 32.

EXAMPLE 60 p-Methoxybenzyl 3-(4-bromo-2-methoxymethyl-3-thienyl)-7β-[2-(2-trityloxyamino-4-thiazolyl)-2-syn-trityliminoacetylamino]-3-cephem-4-carboxylate

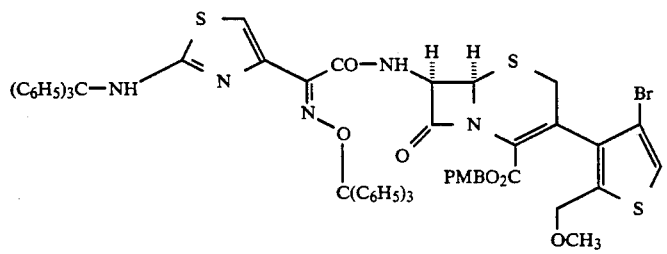

In analogy to the procedure of Example 46, 1.18 g (63% of theory) of the title compound are obtained from 0.85 g (1.6 mmol) of the compound from Example 39.

EXAMPLE 61 p-Methoxybenzyl 7β-[2-(2-amino-4-thiazolyl)-Z-2-butenoylamino]-3-(3-thienyl )-3-cephem-4-carboxylate

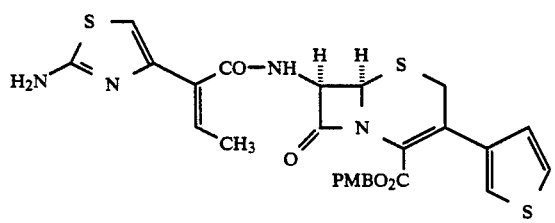

600 mg (1.5 mmol) of the compound from Example 31 and 550 mg (3.0 mmol) of 2-(2-amino-4-thiazolyl )-Z-2-propenecarboxylic acid are stirred overnight at room temperature together with 620 mg (3.0 mmol) of dicyclohexylcarbodiimide in 40 ml of acetonitrile. The precipitate is filtered off with suction, the filtrate is concentrated and the residue is chromatographed on silica gel using toluene/ethyl acetate (1:1).

Yield: 590 mg (69% of theory)

PREPARATION EXAMPLES

EXAMPLE I

7β-[2-(2 -Amino-4-thiazolyl)-2-syn-methoxyimino-acetyl-amino]-3-(2-thienyl)-3-cephem-4-carboxylic acid (trifluoroacetate)

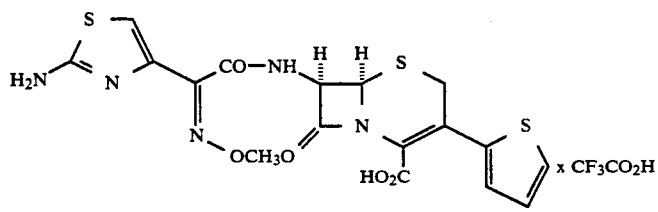

420 mg (0.61 mmol) of the compound from Example 34 are treated at room temperature for 1 h with a mixture of 1 ml of anisole and 50 ml of trifluoroacetic acid. The trifluoroacetic acid is then stripped off in vacuo and the residue is stirred with ether.

Yield: 324 mg (92% of theory)

The following compounds are prepared in analogy to the procedure of Example I:

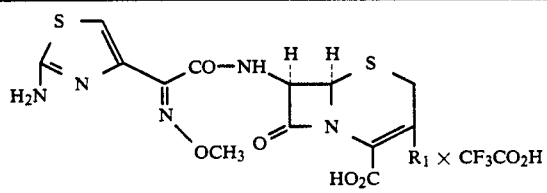

| Example No.: | $R_1$ |
|---|---|
| II |  |
| III | 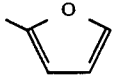 |
| IV | 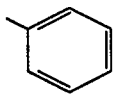 |
| V | 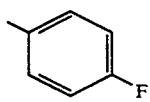 |
| VI | 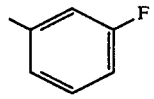 |

-continued

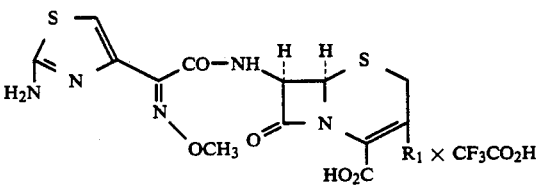

| Example No.: | $R_1$ |
|---|---|
| VII | 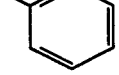 |
| VIII | 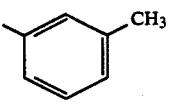 |
| IX | 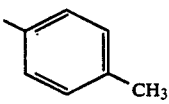 |
| X | 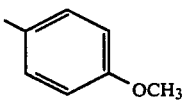 |

EXAMPLE XI

7β-2-(2-Amino-4-thiazolyl)-2-syn-methoxyimino-acetyl-amino]-3-(3-thienyl)-3-cephem-4-carboxylic acid (trifluoroacetate)

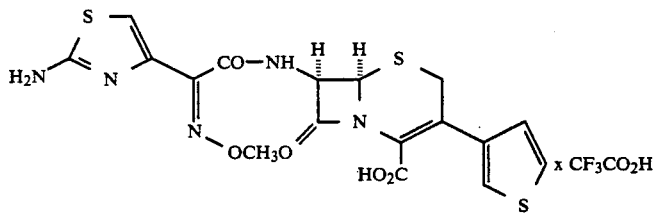

In analogy to the procedure of Example I, 383 mg (66% of theory) of the title compound are obtained from 700 mg (1.0 mmol) of the compound from Example 44.

EXAMPLE XII

7β-[2-(2-Amino-4-thiazolyl)-2-syn-methoxyimino-acetyl-amino]-3-(2-methoxymethyl-3-thienyl)-3-cephem-4-carboxylic acid (trifluoroacetate)

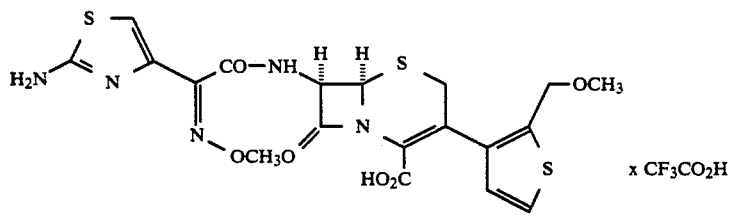

x CF₃CO₂H

In analogy to the procedure of Example I, 30 mg (28% of theory) of the title compound are obtained from 125 mg (0.17 mmol) of the compound from Example 45.

EXAMPLE XIII

7β-[2-(2-Amino-4-thiazolyl)-2-syn-hydroxyimino-acetylamino]-3-(2-thienyl)-3-cephem-4-carboxylic acid

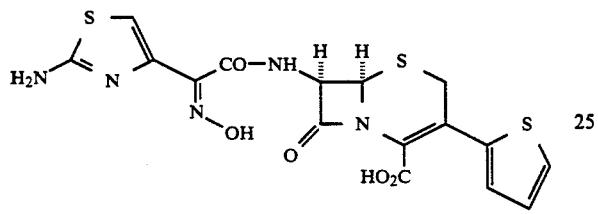

1.1 g (1.0 mmol) of the compound from Example 46 are stirred at room temperature for 1 h with 20 ml of 90% strength formic acid. 1 ml of concentrated hydrochloric acid is then added and the mixture is stirred at room temperature for a further 2 h. It is evaporated to dryness in vacuo and the residue is chromatographed on HP-20 using water/acetonitrile.

Yield: 126 mg (28% of theory)

¹H-NMR (DCOOD): δ=3.90 (s, 2H, 2—H); 5.41 (d, J=5 Hz, 1H, 6—H); 6.08 (d, J=5 Hz, 1H, 7—H); 7.10 (dd, J=5 Hz, J=5 Hz, 1H, 3'—H ); 7.20 ( d, J=5 Hz, 1H, 3'—H); 7.39 (s, 1H, 7'-aryl—H); 7.54 (d, J=5 Hz, 1H, 3'—H).

The following are prepared in analogy to the procedure of Example XIII:

| Example No.: | R₁ |
|---|---|
| XIV | (3-furyl) |
| XV | (2-furyl) |
| XVI | (phenyl) |
| XVII | (4-fluorophenyl) |
| XVIII | (3-fluorophenyl) |
| XIX | (2-fluorophenyl) |
| XX | (3-methylphenyl) |
| XXI | (4-methylphenyl) |
| XXII | (2-methoxyphenyl) |
| XXIII | (3-methoxyphenyl) |
| XXIV | (4-methoxyphenyl) |

EXAMPLE XXV

7β-[2-(2-Amino-4-thiazolyl)-2-syn-hydroxyimino-acetyl-amino]-3-(2-thienyl)-3-cephem-4-carboxylic acid

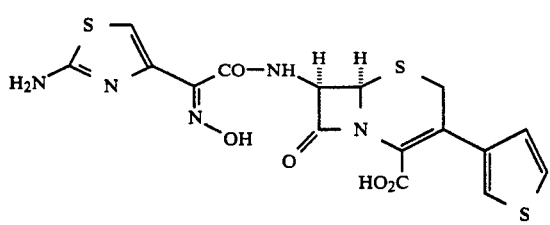

In analogy to the procedure of Example XXIII, 572 mg (89% of theory) of the title compound are obtained from 1.50 g (1.42 mmol) of the compound from Example 16.

EXAMPLE XXVI

7β-[2-(2-Amino-4-thiazolyl)-2-syn-hydroxyimino-acetyl-amino]-3-(2-methoxymethyl-3-thienyl)-3-cephem-4-carboxylic acid

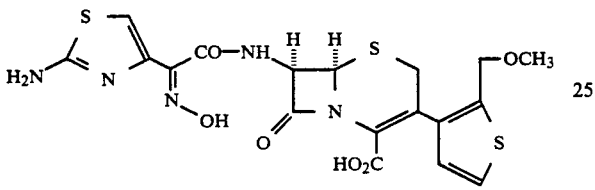

In analogy to the procedure of Example XIII, 28 mg (7% of theory) of the title compound are obtained from 700 mg (0.64 mmol) of the compound from Example 59.

EXAMPLE XXVII

7β-[2-(2-Amino-4-thiazolyl)-2-syn-hydroxyimino-acetyl-amino]-3-(4-bromo-2-methoxymethyl-3-thienyl )-3-cepham-4-carboxylic acid

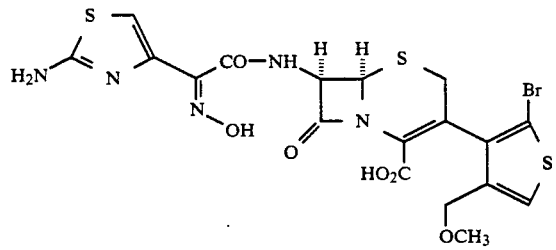

In analogy to the procedure of Example XIII, 580 rag (91% of theory) of the title compound are obtained from 1.10 g (0.93 mmol) of the compound from Example 60.

EXAMPLE XXVIII

7β-[2-(2-Amino-4-thiazolyl )-Z-2-butenoylamino]-3-(3-thienyl)-3-cephem-4-carboxylic acid (sodium salt)

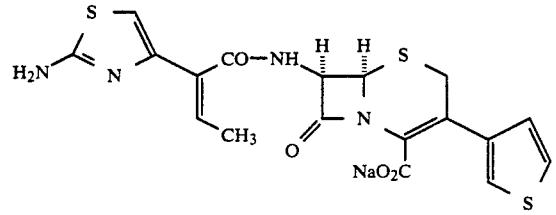

$^1$H—NMR (DCOOD): δ=2.10 (d, J=7 Hz, 3H, CH$_3$); 3.83 and 3.91 (2d, J=18 Hz, each 1H, 2—H); 5.40 ( d, J=6 Hz, 1H, 6—H); 6.04 (d, J=6 Hz, 1H, 7—H); 6.60 (q, J=7 Hz, 1H, 7'—CH); 6.86 (s, 1H, 7'—aryl—H); 7.14 (m, 1H, 3'—H); 7.48 (m, 2H, 3'—H).

We claim:

1. A compound of the formula

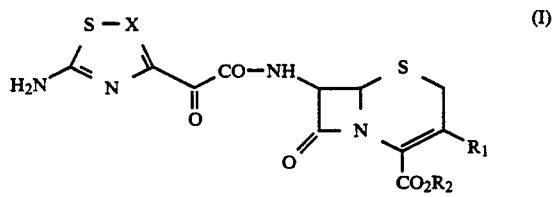

in which

X represents a nitrogen atom or the —CH group,

Y represents a group of the formula N—OR$_3$ or CHR$_4$, in which

R$_3$ denotes hydrogen, straight-chain or branched alkenyl, alkinyl or alkyl in each case having up to 8 carbon atoms, where the latter can optionally be substituted by halogen or by protected or unprotected carboxyl or amino, R$_4$ denotes hydrogen, aryl having 6 to 10 carbon atoms, protected or unprotected carboxyl, halogen or straight-chain or branched alkoxycarbonyl, alkoxy, alkenyl or alkyl in each case having up to 8 carbon atoms, where the latter can be substituted by halogen, hydroxyl, nitro, cyano, carboxyl or by straight-chain or branched alkoxy or alkoxycarbonyl in each case having up to 6 carbon atoms, R$_1$ represents thienyl or furyl which is optionally monosubstitutecd to trisubstituted by identical or different halogen, trifluoromethyl, trifluoromethoxy or hydroxy substituents or by a group of the formula —NR$_4$R$_6$ in which R$_5$ and R$_6$ are identical or different and denote hydrogen, straight-chain or branched alkyl having up to 8 carbon atoms or phenyl, or are substituted by straight-chain or branched alkoxy or alkyl in each case having up to 8 carbon atoms, where the latter can be substituted by hydroxy, halogen or by straight-chain or branched alkoxy having up to 6 carbon atoms, R$_2$ represents hydrogen, or represents a carboxyl protecting group or represents an ester radical which can be cleaved in vivo, or a pharmaceutically tolerable salt thereof.

2. A compound or salt thereof according to claim 1, in which R$_2$ represents

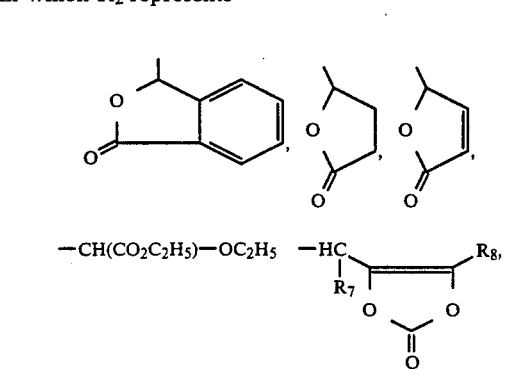

-continued

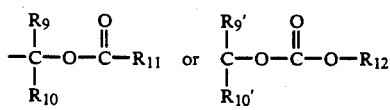

in which

R$_7$ and R$_8$ are identical or different and denote hydrogen, phenyl or straight-chain or branched alkyl having up to 4 carbon atoms, R$_9$, R$_{9'}$, R$_{10}$ and R$_{10'}$ are identical or different and denote hydrogen or straight-chain or branched alkyl having up to 4 carbon atoms, R$_{11}$ denotes straight-chain or branched alkyl having up to 6 carbon atoms, R$_{12}$ denotes straight-chain or branched alkyl having up to 6 carbon atoms or cyclohexyl.

3. A compound or salt thereof according to claim 1, in which

X represents a nitrogen atom or the —CH group,

Y represents a group of the formula N—OR$_3$ or CH—R$_4$, in which

R$_3$ denotes hydrogen or straight-chain or branched alkyl having up to 6 carbon atoms, which is optionally substituted by fluorine, chlorine, bromine or protected or unprotected carboxyl or amino, R$_4$ denotes hydrogen, phenyl, carboxyl, fluorine, chlorine, bromine or straight-chain or branched alkoxy, alkoxycarbonyl or alkyl in each case having up to 6 carbon atoms, where the latter can be substituted by fluorine, chlorine, bromine, hydroxyl, carboxyl or by straight-chain or branched alkoxy or alkoxycarbonyl in each case having up to 4 carbon atoms, R$_1$ represents thienyl or furyl which is optionally monosubstituted or disubstutited by identical or different fluorine, chlorine or bromine substituents, or by a group of the formula —NR$_5$R$_6$, in which R$_5$ and R$_6$ are identical or different and denote hydrogen or straight-chain or branched alkyl having up to 6 carbon atoms, or are substituted by straight-chain or branched alkoxy or alkyl in each case having up to 6 carbon atoms, where the latter can be substituted by hydroxyl, fluorine, chlorine or by straight-chain or branched alkoxy having up to 4 carbon atoms, R$_2$ represents hydrogen, or represents methyl, ethyl, tert-butyl, 2-chloroethyl, 2,2,2-trichloroethyl, cyanoethyl, diphenylmethyl, triphenylmethyl, acetoxymethyl, allyl, benzyl, 4-methoxybenzyl, 2,4-dimethoxybenzyl, 1-phenoxyethyl, 2-methyl-2-propenyl, 4-nitrobenzyl, 2-nitrobenzyl, trimethylsilylethyl or tert-butyl-dimethylsilylethyl, or represents a radical of the formula

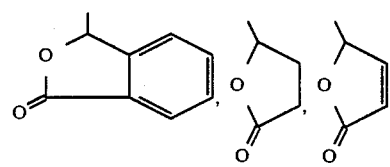

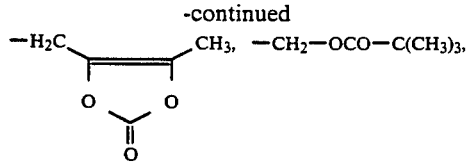

—CH(CH$_3$)—OCOOC$_2$H$_5$, —CH$_2$—OCOCH$_3$,

—CH—(CH$_3$)—O—CO—CH$_3$, —CH(CH$_3$)—O—COO—CH$_3$,

—CH(CH$_3$)—O—COO—CH(CH$_3$)$_2$,

—CH(CH$_3$)—O—COO—C$_6$H$_{11}$ or —CH(CO$_2$C$_2$H$_5$)—OC$_2$H$_5$.

4. A compound or salt thereof according to claim 1, in which

X represents a nitrogen atom or the —CH group,

Y represents a group of the formula N—OR$_3$ or —CHR$_4$, in which

R$_3$ denotes hydrogen or straight-chain or branched alkyl having up to 4 carbon atoms, which is optionally substituted by fluorine, chlorine or by protected or unprotected carboxyl or amino, R$_4$ denotes hydrogen or straight-chain or branched alkoxy or alkyl in each case having up to 4 carbon atoms, where the latter can be substituted by hydroxyl, carboxyl, methoxy, ethoxy or propoxy, R$_1$ represents thienyl or furyl which is optionally monosubstituted or disubstituted by identical or different fluorine, chlorine, bromine or amino substituents or by straight-chain or branched alkoxy, alkoxycarbonyl or alkyl in each case having up to 4 carbon atoms, where the latter can be substituted by hydroxy, fluorine, chlorine, methoxy or ethoxy, R$_2$ represents hydrogen, or represents a radical of the formula

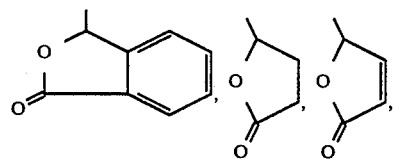

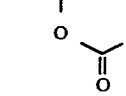

—CH(CH$_3$)—OCOOC$_2$H$_5$, —CH$_2$—OCOCH$_3$,

—CH—(CH$_3$)—O—CO—CH$_3$, —CH(CH$_3$)—O—COO—CH$_3$,

—CH(CH$_3$)—O—COO—CH(CH$_3$)$_2$,

—CH(CH$_3$)—O—COO—C$_6$H$_{11}$ or —CH(CO$_2$C$_2$H$_5$)—OC$_2$H$_5$.

5. A compound of salt thereof according to claim 1, in which

R$_1$ represents thienyl or furyl which is optionally monosubstituted to trisubstituted by identical or different halogen, trifluoromethyl, trifluoromethoxy or hydroxyl substituents or by a group of the formula —NR$_5$R$_6$.

6. A compound or salt thereof according to claim 1, in which

R$_1$ represents a member selected from the group consisting of furyl, thienyl, methoxymethylthienyl, methoxymethyl-bromo-thienyl.

7. A compound or salt thereof according to claim 6, in which

X represents the —CH group, and
Y represents =N—OH, =N—OCH$_3$ or =CH—CH$_3$.

8. An antibacterial composition comprising an antibacterially effective amount of a compound or salt according to claim 1 and a pharmaceutically tolerable diluent.

9. A method of combating bacterial infection in a patient in need thereof which comprises administering to such patient an antibacterially effective amount of a compound or salt according to claim 1.

* * * * *

UNITED STATES PATENT AND TRADEMARK OFFICE
CERTIFICATE OF CORRECTION

PATENT NO. : 5,324,721
DATED : June 28, 1994
INVENTOR(S) : Stephan Schneider, et. al.

It is certified that error appears in the above-identified patent and that said Letters Patent is hereby corrected as shown below:

Column 28, lines 10-15, cancel the structure

"
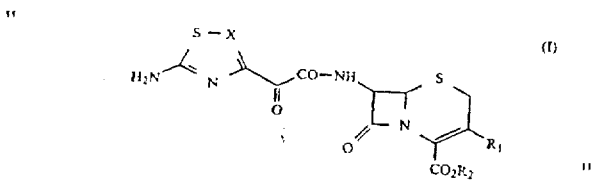
"

and substitute

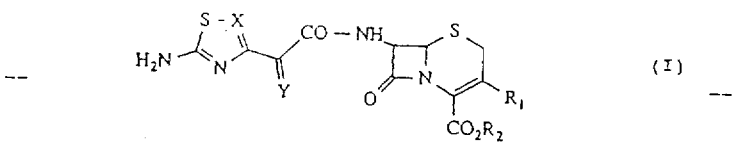

--

UNITED STATES PATENT AND TRADEMARK OFFICE
CERTIFICATE OF CORRECTION

PATENT NO. : 5,324,721
DATED : June 28, 1994
INVENTOR(S) : Stephan Schneider, et. al.

It is certified that error appears in the above-indentified patent and that said Letters Patent is hereby corrected as shown below:

Column 28, line 40, cancel "--$NR_4R_6$" and substitute -- --$NR_5$-$R_6$--

Column 28, lines 46-47, cancel "hydroxy" and substitute --hydroxyl--

Signed and Sealed this

Thirtieth Day of November, 1999

Attest:

Q. TODD DICKINSON

Attesting Officer

Acting Commissioner of Patents and Trademarks